United States Patent [19]

Stanko

[11] Patent Number: 5,134,162

[45] Date of Patent: Jul. 28, 1992

[54] METHOD FOR LOWERING HIGH BLOOD CHOLESTEROL LEVELS IN HYPERLIPIDEMIC ANIMALS AND CONFECTIONS AS THE INGESTION MEDIUM

[75] Inventor: Ronald T. Stanko, Pittsburgh, Pa.

[73] Assignee: The Montefiore Hospital Association of Western Pennsylvania, Pittsburgh, Pa.

[21] Appl. No.: 632,936

[22] Filed: Dec. 24, 1990

[51] Int. Cl.$^5$ ............... A61K 31/19; A61K 47/00; A61K 9/68

[52] U.S. Cl. ................... 514/557; 514/948; 424/439; 424/440

[58] Field of Search ............. 514/557, 948; 424/439

[56] References Cited

U.S. PATENT DOCUMENTS 4,351,835  9/1982  Stanko ................... 514/251

Primary Examiner—Frederick E. Waddell
Assistant Examiner—Kimberly R. Jordan
Attorney, Agent, or Firm—Harry B. Keck

[57] ABSTRACT

A process for lowering the blood cholesterol of hyperlipidemic patients by oral ingestion of pyruvate and a confection (cereal bar, fruit bar, candy) containing pyruvate as the ingestion medium.

12 Claims, No Drawings

METHOD FOR LOWERING HIGH BLOOD CHOLESTEROL LEVELS IN HYPERLIPIDEMIC ANIMALS AND CONFECTIONS AS THE INGESTION MEDIUM

BACKGROUND OF THE INVENTION

1. Field of the Invention

The present invention provides a method for lowering high blood cholesterol levels in hyperlipidemic animals, and more particularly, feeding such hyperlipidemic animals a therapeutically effective amount of pyruvate to accomplish the objective. The invention also concerns confections containing pyruvate as media for ingesting the pyruvate.

In human patients, blood cholesterol levels range from 120 to 330, measured as milligrams of cholesterol in a deciliter of blood (mg/dl). High blood cholesterol is a subjective determination. High levels of blood cholesterol are a risk factor for developing heart disease when accompanied by high blood pressure, obesity, organic heart disease or a family history of organic heart disease, diabetes, smoking (tobacco), and in patients who have recently survived heart attacks. The age, medical history and condition of each patient must be reviewed before determining what constitutes a "high" level of blood cholesterol for that patient. For example, in a healthy patient, less than 30 years old with no significant medical history, a blood cholesterol level above 200 mg/dl might be considered "high" and a patient is a candidate for treatment. In a healthy patient 20 to 40 years old with no significant medical history, a blood cholesterol level above 220 mg/dl might be considered "high". In a healthy patient 40 to 50 years old, with no significant medical history, a blood cholesterol level above 250 mg/dl might be considered "high". In any patient, blood cholesterol levels above 250 mg/dl are usually considered to be "high" and appropriate for treatment.

2. Description of the Prior Art

Hyperlipidemic patients exhibit high blood cholesterol levels and are considered to be in jeopardy of various circulatory diseases, diabetes and heart attacks.

Pyruvate and mixtures of pyruvate with dihydroxyacetone have been described for a number of beneficial results:

U.S. Pat. No. 4,158,057 describes oral administration of pyruvate and dihydroxyacetone to prevent excessive accumulation of fatty deposits in a mammal liver due to ethanol ingestion.

U.S. Pat. No. 4,351,835 describes oral administration of pyruvate and dihydroxyacetone to reduce an expected weight gain from a given diet or to induce a weight loss in a mammal. The patent also describes oral administration of pyruvate and dihydroxyacetone to athletes prior to strenuous athletic events to increase endurance and/or performance.

U.S. Pat. No. 4,415,575 describes oral administration of pyruvate and dihydroxyacetone to increase the body protein concentration in a mammal.

U.S. Pat. No. 4,458,937 describes oral administration of pyruvate to a mammal to induce a weight loss or reduce an expected weight gain from a given diet.

U.S. Pat. No. 4,645,764 describes oral administration to a living being of pyruvate and dihydroxyacetone to induce a weight loss or to reduce an expected weight gain from a given diet and for inhibiting body fat while increasing body protein concentration.

U.S. Pat. No. 4,812,478 describes oral administration of dihydroxyacetone to an animal to induce a weight loss or to reduce an expected weight gain from a given diet.

Copending patent application Ser. No. 232,118, filed Aug. 15, 1988, describes the use of pyruvate and dihydroxyacetone for increasing the glucose uptake in the muscles of an animal. Application Ser. No. 232,118 has been abandoned and replaced with continuation application Ser. No. 546,680, filed Jul. 5, 1990.

These described results of oral administration of pyruvate and pyruvate with dihydroxyacetone are of great interest for medical patients who ingest ethanol; medical patients having fatty liver deposits or tendencies toward fatty liver deposits; medical patients who are obese or have a tendency toward obesity; normal subjects desiring to lose body weight or to retard body weight increase; normal patients, particularly athletes, who desire to increase endurance; and medical patients having diabetic tendencies.

STATEMENT OF THE PRESENT INVENTION

According to this invention I have discovered that high blood cholesterol levels of hyperlipidemic patients can be lowered when the patients receive oral administration of pyruvate.

The pyruvate portion of the patient's diet will be from 2 to 15 percent of the total calories in the diet. The treatment is most effective when the hyperlipidemic patient is on a low fat, weight maintenance diet for sub-weight maintenance (reducing) diet. The pyruvate may be mixed as an additive with other foods and preferably is included in all or most of the patient's meals. Alternatively the pyruvate may be incorporated in candy such as hard-coated chocolate or mint pellets, cereal bars (e.g. molded granola with fruits) etc. Typically the calorie content of the pyruvate will comprise 2 to 15 percent of the total calories in the patient's diet.

A convenient medium for administering the pyruvate is a confection containing 2 to 20 weight percent pyruvate. Such confections may be candy, cereal bars, fruit bars and similar food products which are customarily consumed between scheduled or planned meals. The confection should be one in which the pyruvate is not heated above 180° F. Candy such as chocolate bonbons, hard-candy coated chocolate, nut-filled chocolates, fruit or mint jellies or fruits or hard candies are preferred. Snack bars comprising coated raw or partially cooked cereal grains and/or fruits and/or nuts also are useful as an ingestion medium.

DESCRIPTION OF THE PREFERRED EMBODIMENTS

A group of 39 human subjects was assembled for outpatient treatment over an observation period of six weeks. All of the subjects were hyperlipidemic patients having high blood cholesterol levels, both plasma cholesterol (greater than 240 mg/dl) and LDL cholesterol (greater than 150 mg/dl). The subjects were divided into a placebo group (20 subjects) and a treatment group (19 subjects). Both groups received a weight maintenance diet throughout the evaluation period containing 35-40 percent of the calories in the form of normal fat and containing normal cholesterol of 400-500 milligrams/day. A weight maintenance diet contains 28 to 30 calories per kilogram of weight.

The Placebo Group—The 20 subjects of the placebo group included 16 female patients and 4 male patients having an average weight 76.3±3.9 kilograms and an average age of 54.8±2.8 years. The placebo group received 7% of the carbohydrate calories in the form of Polycose ™, which is a solution of glucose, i.e., 19 to 32 grams daily.

Treatment Group—The 19 subjects of the treatment group included 15 female patients and 4 male patients having an average weight of 80.4±5.2 kilograms and an average age of 56.3±2.5 years. The treatment group received 7% of the carbohydrate calories in the form of pyruvate, i.e., 26 to 44 grams daily.

A statistically significant reduction in the total blood cholesterol was observed after six weeks in the treatment group whereas zero change was observed in the placebo group. The results are summarized in the following TABLE 1.

TABLE 1

RESULTS OF SIX WEEKS EVALUATION OF SUBJECTS HAVING HIGH BLOOD CHOLESTEROL LEVELS

| | PLACEBO GROUP | TREATMENT GROUP |
|---|---|---|
| Total Subjects | 20 | 19 |
| Males | 4 | 4 |
| Females | 16 | 15 |
| Average Weight (kilograms) | 76.3 ± 3.9 | 80.4 ± 5.2 |
| Average Age (years) | 54.8 ± 2.8 | 56.3 ± 2.5 |
| Total Cholesterol | | |
| In Plasma (start) mg/dl | 265 ± 7 | 275 ± 7 |
| LDL Cholesterol (start) mg/dl | 175 ± 7 | 186 ± 7 |
| Total Cholesterol | | |
| In Plasma (ater 6 weeks) mg/dl | 265 ± 7 | 264 ± 7 |
| LDL Cholesterol (after 6 weeks) mg/dl | 175 ± 7 | 176 ± 7 |
| Change in Cholesterol | | |
| In Plasma mg/dl | 0 | −11 |
| LDL Cholesterol mg/dl | 0 | −10 |
| Percentage Change in Cholesterol | | |
| In Cholesterol | 0 | −4%* |
| LDL Cholesterol | 0 | −5.4%* |

*Standard deviation <0.05 compared to placebo values.

The standard deviation ($p = <0.05$) indicates that the reported results are statistically significant.

For hyperlipidemic patients weighing from 110 to 250 pounds, an effective dosage of pyruvate is from about 10 to about 50 grams per day as a substitute for other carbohydrate nutrients in the patient's diet.

Preferably the calorie content of the pyruvate comprises 2 to 15 percent of the total calories in the diet.

I claim:

1. A method for treating a hyperlipidemic animal to lower the blood total cholesterol level of that animal which comprises administering orally to the animal a therapeutically effective amount of pyruvate whereby the blood total cholesterol level of the animal becomes lower than that if the animal had not received said amount.

2. A method for treating a hyperlipidemic animal to lower the LDL cholesterol level of that animal which comprises administering orally to the animal a therapeutically effective amount of pyruvate whereby the LDL cholesterol level of the animal becomes lower than that if the animal had not received said amount.

3. The method of claim 1 where the amount of pyruvate is from 10 to 50 grams per day.

4. The method of claim 2 where the amount of pyruvate is from 10 to 50 grams per day.

5. The method of claim 1 wherein the calories derived from pyruvate comprises 2 to 15 percent of the total calories in the animal's diet.

6. The method of claim 2 wherein the calories derived from pyruvate comprises 2 to 15 percent of the total calories in the animal's diet.

7. The method of claim 1 wherein a portion of the pyruvate is administered orally in the form of a confection containing pyruvate.

8. The method of claim 1 wherein a portion of the pyruvate is administered in the form of cereal bars containing pyruvate.

9. A confection comprising a confection-like carrier containing 2 to 20 percent by weight pyruvate.

10. The confection of claim 9 comprising a cereal bar containing raw, uncooked cereal grains.

11. The confection of claim 9 comprising a fruit bar containing raw or cooked fruit.

12. The confection of claim 9 comprising a candy.

* * * * *